(12) United States Patent
Dorward

(10) Patent No.: US 6,855,897 B1
(45) Date of Patent: Feb. 15, 2005

(54) WATER TREATMENT APPARATUS AND COMPONENTS

(75) Inventor: Donald Charles Dorward, Southport (AU)

(73) Assignee: AquaPlus Technologies Pty., Ltd., Bundall (AU)

( * ) Notice: Subject to any disclaimer, the term of this patent is extended or adjusted under 35 U.S.C. 154(b) by 0 days.

(21) Appl. No.: 09/743,645
(22) PCT Filed: Jul. 15, 1999
(86) PCT No.: PCT/AU99/00572
§ 371 (c)(1),
(2), (4) Date: Jan. 9, 2001
(87) PCT Pub. No.: WO00/03953
PCT Pub. Date: Jan. 27, 2000

(30) Foreign Application Priority Data

Jul. 17, 1998 (AU) .............................................. PP4741

(51) Int. Cl.[7] ............................ H01H 35/06; G01F 3/14
(52) U.S. Cl. ................... 200/81.9 R; 73/239; 200/82 R; 210/87
(58) Field of Search ...................... 200/81.9 R, 81.9 M, 200/82 E, 82 R, 238, 239; 210/97, 137, 223, 243, 259, 87; 340/606, 618; 73/861.08, 239, 242

(56) References Cited

U.S. PATENT DOCUMENTS

| | | | | |
|---|---|---|---|---|
| 3,963,889 A | * | 6/1976 | Stonich | 200/81.9 R |
| 4,763,114 A | * | 8/1988 | Eidsmore | 340/606 |
| 4,879,440 A | * | 11/1989 | Lymburger | 200/82 R |
| 4,996,396 A | * | 2/1991 | Smith | 200/81.9 M |
| 5,070,220 A | * | 12/1991 | Glenn | 200/87.9 M |
| 5,114,571 A | * | 5/1992 | Pier et al. | 210/243 |

* cited by examiner

Primary Examiner—Joseph Drodge
(74) Attorney, Agent, or Firm—Paul F. McQuade; James E. Goepel; Greenberg Traurig, LLP (57) ABSTRACT

A portable water treatment apparatus including: a pump, a coarse filter means, an adsorbent filter means, a fine filter means, a silver ion generator downstream of the pump and in series with the adsorbent filter and control means for controlling the operation of said first silver generator whereby said silver ion generator discharges silver ions into the water at a predetermined rate and in response to a predetermined flow rate, said control means including a flow switch.

4 Claims, 6 Drawing Sheets

FIG. 7

WATER TREATMENT APPARATUS AND COMPONENTS

TECHNICAL FIELD OF THE INVENTION

This invention relates to apparatus for the treatment of water for human consumption and the destruction or removal of bacteria and other micro-organisms which are dangerous to health, and components for such apparatus.

BACKGROUND ART

It is relatively well known that silver ions (Ag+) in measured doses are toxic to lower life forms such as bacteria but are non-toxic to humans. In fact there is evidence available that silver provides significant benefits to the functioning of the human body and offers particular benefits to the immune system. Various types of apparatus are presently available for dosing water with silver ions in order to take advantage of the bactericide effects of silver and typically such apparatuses include a flow switch which activates a silver ion generator upon a person turning on a tap for a glass of water. Generally, apparatuses of this type have been used only in reticulated water systems, for example, where town water is connected and is already relatively clean and reasonably safe.

The steady growth of tourism in outback areas has placed an undesirable burden on government authorities to provide safe drinking and bathing water in such areas for the benefit of tourists and holiday makers. However, the provision of such facilities decreases the appeal of the outback and the ability of tourists and holiday makers to camp where they like. Moreover any facilities provided could possibly be destroyed or rendered ineffective by vandals. Additionally there are many areas which are so little used and so remote that government authorities are unable to provide and maintain the necessary facilities particularly in developing nations and jungle areas. Furthermore, even if presently available apparatus were to be used in remote areas, in some cases they do not control the growth of harmful bacteria downstream of the apparatus to a satisfactory extent.

One object of the present invention is to provide water treatment apparatus which controls or at least inhibits the growth of harmful bacteria downstream of the apparatus and which can be used in outback areas and/or with reticulated water supplies to improve water quality or at least decrease the possibility of harmful bacteria being consumed. Another object is to provide portable water treatment apparatus which will allow holiday makers and others, especially those with four wheel drive vehicles, to sterilise and filter water from streams, water holes, dams and the like thus converting it to potable water for drinking and washing. Another object is to provide an improved flow switch which can be used for activating a silver ion generator in water treatment apparatus of the type herein described.

DISCLOSURE OF THE INVENTION

With the foregoing in view the invention in one aspect resides broadly in portable water treatment apparatus including:

a base and a handle operatively connected to said base by which a person may carry the apparatus;

pump means operatively mounted to said base, said pump means including a water inlet and a water outlet;

coarse filter means upstream of said pump means for filtering undesirably large solids from the water prior to entering said water inlet and a flexible conduit connected to said coarse filter means for providing a flow path for the water to said coarse filter means;

adsorbent filter means downstream of said pump means for removing undesirable odours, tastes and chemical pollutants such as chlorine, trichloromethanes, herbicides, pesticides and the like from the water;

fine filter means downstream of said pump means and in series with said adsorbent filter means for removing organisms of the protozoan group particularly amoeba, giardia, and cryptospiridium from the water;

a first silver ion generator downstream of said pump means and in series with said adsorbent filter means and said fine filter means for releasing silver ions into water inflowing from said pump outlet;

control means for controlling the operation of said first silver ion generator whereby said silver ion generator discharges silver ions into the water at a predetermined rate and in response to a predetermined flow rate, said control means including a flow switch;

flow regulating means downstream of said pump means and in series with said adsorbent filter means, said fine filter means and said first silver ion generator for regulating the rate of flow of water from said pump outlet;

connection means for connecting a battery type power supply to said pump means and/or said silver ion generator, and cover means removably attached to said base means for covering or at least partially covering said pump means, said coarse filter means, said adsorbent filter means, said fine filter means and said first silver ion generator. Preferably, the portable water treatment apparatus also includes a second silver ion generator downstream of said adsorbent filter means and said fine filter means for releasing silver ions into the filtered water. It is also preferred that said first silver ion generator be located upstream of said adsorbent filter means.

In another aspect the invention resides broadly in water treatment apparatus including:

a mounting base adapted to be secured to a wall for mounting the apparatus near a water supply outlet;

filter means mounted to said mounting base and adapted to be connected to the water supply outlet, said filter means including adsorbent filter means for removing undesirable odours, tastes and chemical pollutants such as chlorine, trichloromethanes, herbicides, pesticides and the like from the water and fine filter means in series with said adsorbent filter means for removing organisms of the protozoan group particularly amoeba, giardia and cryptospiridium from the water;

a first silver ion generator upstream of said adsorbent filter means and said fine filter means for releasing silver ions into water inflowing from said water supply outlet;

a second silver ion generator downstream of said adsorbent filter means and said fine filter means for releasing silver ions into the filtered water;

control means for controlling the operation of said first and second silver ion generators whereby said silver ion generators discharge silver ions into the water at a predetermined rate and in response to a predetermined flow rate, said control means including a flow switch;

flow regulating means in series with said adsorbent filter means, said fine filter means and said first and second dosing means for regulating the rate of flow of water through said first and second dosing units;

connection means for connecting a power supply to said first and second dosing means. Advantageously, the second silver ion generator ensures that sufficient silver ions are available for destroying any bacteria in drinking vessels or the like into which the treated water is discharged and also decreases the possibility of contamination of any pipework or fittings downstream via back entry. The second silver ion generator is particularly advantageous with the portable apparatus because of the likelihood of back contamination in a bush environment.

Preferably, the adsorbent filter means is a carbon filter which is selected to retain therein at least some silver ions. It is believed that a 5 micron rating is suitable for this purpose. When the first silver ion generator is located upstream of the adsorbent filter it is believed that at least some of the silver ions become lodged in the carbon filter thus preventing the growth of harmful bacteria in the filter.

Preferably, the fine filter means is a ceramic filter which is selected to prevent the passage of protozoans and undesirable metal particulates such as lead. It is believed that a 4 micron rating is suitable. It is also preferred that the fine filter means be located downstream of said adsorbent filter means and said dosing means. In this respect it is believed that the ceramic filter can be appropriately sized to prevent the passage of pathogenic bacteria for a short period in the event of failure of one or both silver ion generators.

Preferably, the adsorbent filter means and the fine filter means are suitably sized to provide a reservoir of water which has been dosed with silver ions so that water will remain in the system for a sufficient time for all harmful bacteria to be destroyed by the silver ions. In the case of the portable apparatus it is also preferred that a foot valve or non-return valve be located upstream of the pump means for preventing backflow of treated or semi-treated water from the apparatus.

Preferably the flow regulating means is adjustable so as to restrict the flow rate of water through the apparatus so that water remains in the apparatus for a predetermined period greater that the minimum time required for destruction of harmful bacteria.

In another aspect the invention resides broadly in a flow switch including:

a body having an inlet passage and an outlet passage;

a reed and a contact mounted in said body downstream of said inlet passage, said reed being adapted for oscillating movement towards and away from said contact into and out of engagement therewith, and said reed and said contact being constructed of electrically conductive material;

a piston mounted in said inlet passage for sliding movement along said inlet passage towards and away from said reed, said piston having an upstream end and a downstream end, and a flow passage in said piston, said flow passage having an inlet at or adjacent the upstream end and an outlet intermediate said upstream end and said downstream end, the parts being so made and arranged that fluid entering said inlet passage will cause said piston to move in said inlet passage and engage with said reed forcing said reed into electrically conductive engagement with said contact and will flow through said flow passage and be discharged sidewardly of said piston in said body downstream of said inlet passage for discharge through said outlet passage.

Preferably, the piston has a tapered portion adjacent the downstream end and the flow passage outlet is located in the tapered portion. Advantageously, locating the flow passage outlet in this manner ensures that flow through the flow passage outlet is not unduly restricted by the wall of the inlet passage.

Preferably, the body is substantially a rectangular prism in form with a single cylindrical passage therethrough with one end portion forming the inlet passage and the other end portion forming the outlet passage. It is also preferred that the cylindrical passage be provided in one half of the body so that fixing apertures may be provided in the other half of the body without the risk of opening into the cylindrical passage.

BRIEF DESCRIPTION OF THE DRAWINGS

In order that this invention may be more readily understood and put into practical effect, reference will now be made to the accompanying drawings wherein.

DETAILED DESCRIPTION OF THE DRAWINGS

The water treatment apparatus 10 illustrated in FIGS. 1 to 5 has a mounting base 11 with an upstanding central partition 12 which terminates centrally in a handle 13. A cover 14 is attached to the base by clips 16 on each side of the cover and the handle 13 is accessible through an aperture 17 in the top 18 of the cover. It will be seen that the apparatus is a compact unit which can be easily stowed in the stowage compartment of a four wheel drive vehicle or even the boot of a car.

Figure 1:
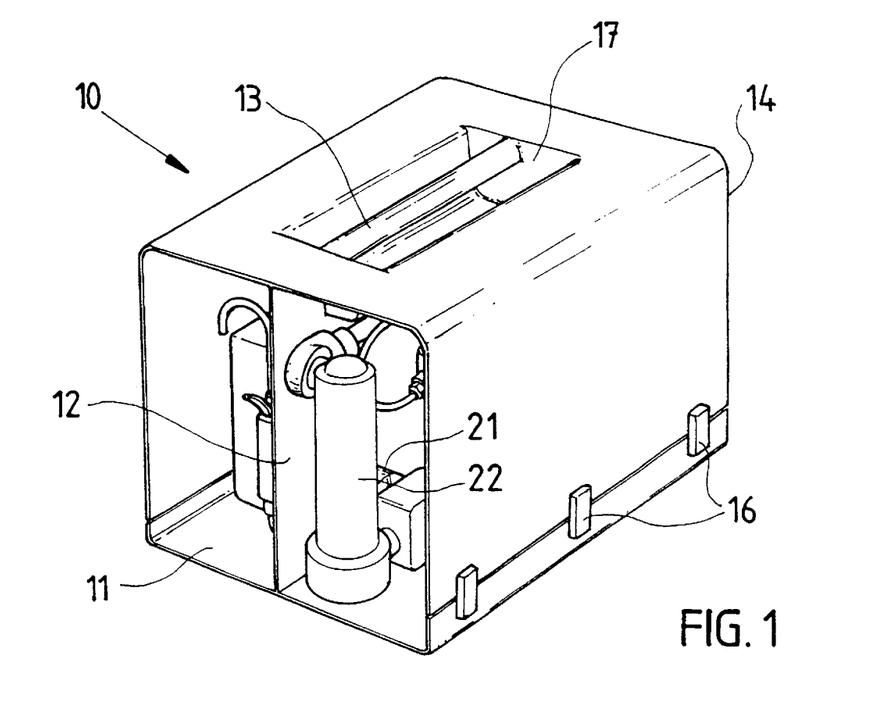
FIG. 1 is a pictorial representation of portable water treatment apparatus according to the invention.
Figure 2:
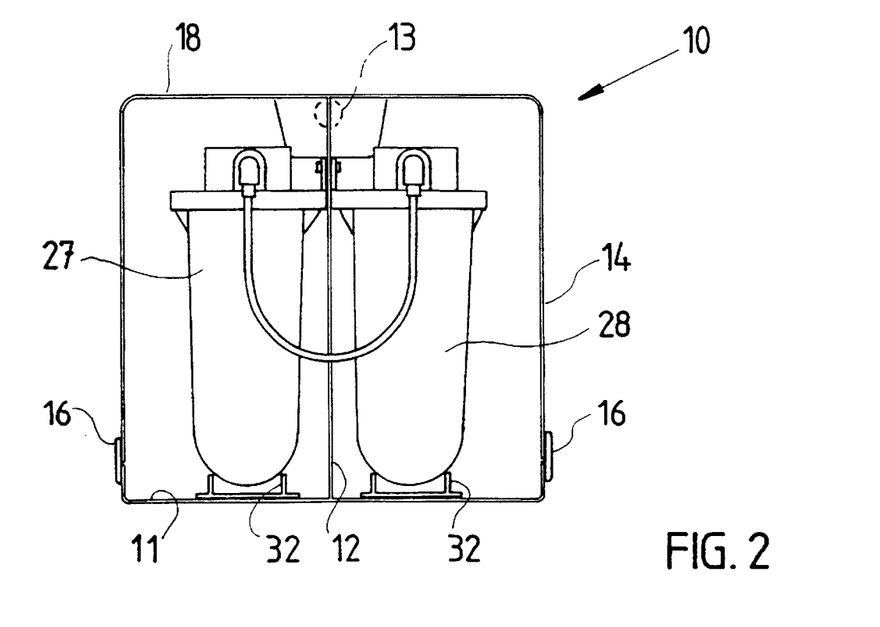
FIG. 2 is a rear end elevation of the apparatus of FIG. 1.
Figure 3:
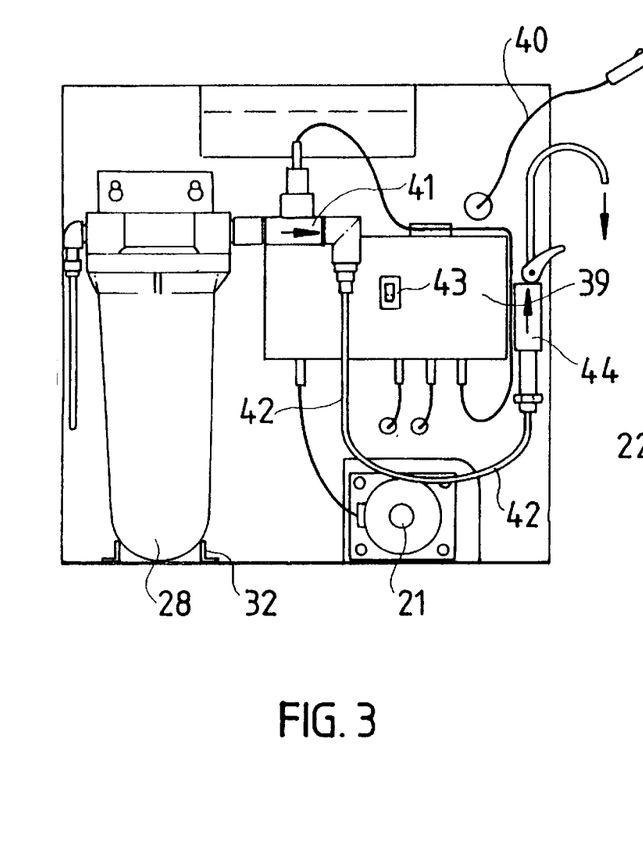
FIG. 3 is an elevation of one side of the apparatus of FIG. 1 with the cover removed.
Figure 4:
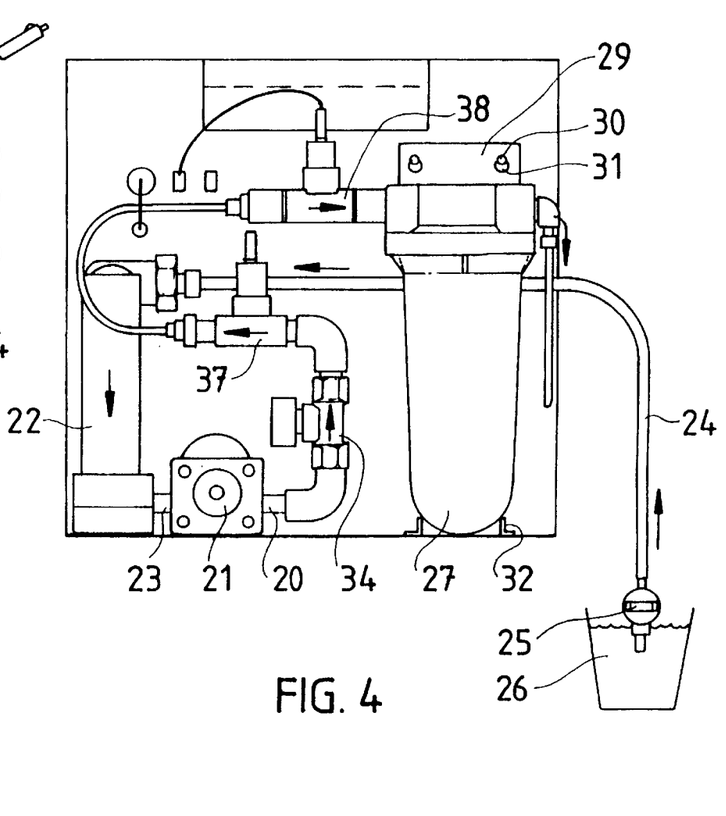
FIG. 4 is an elevation of the other side of the apparatus of FIG. 1 with the cover removed.
Figure 5:
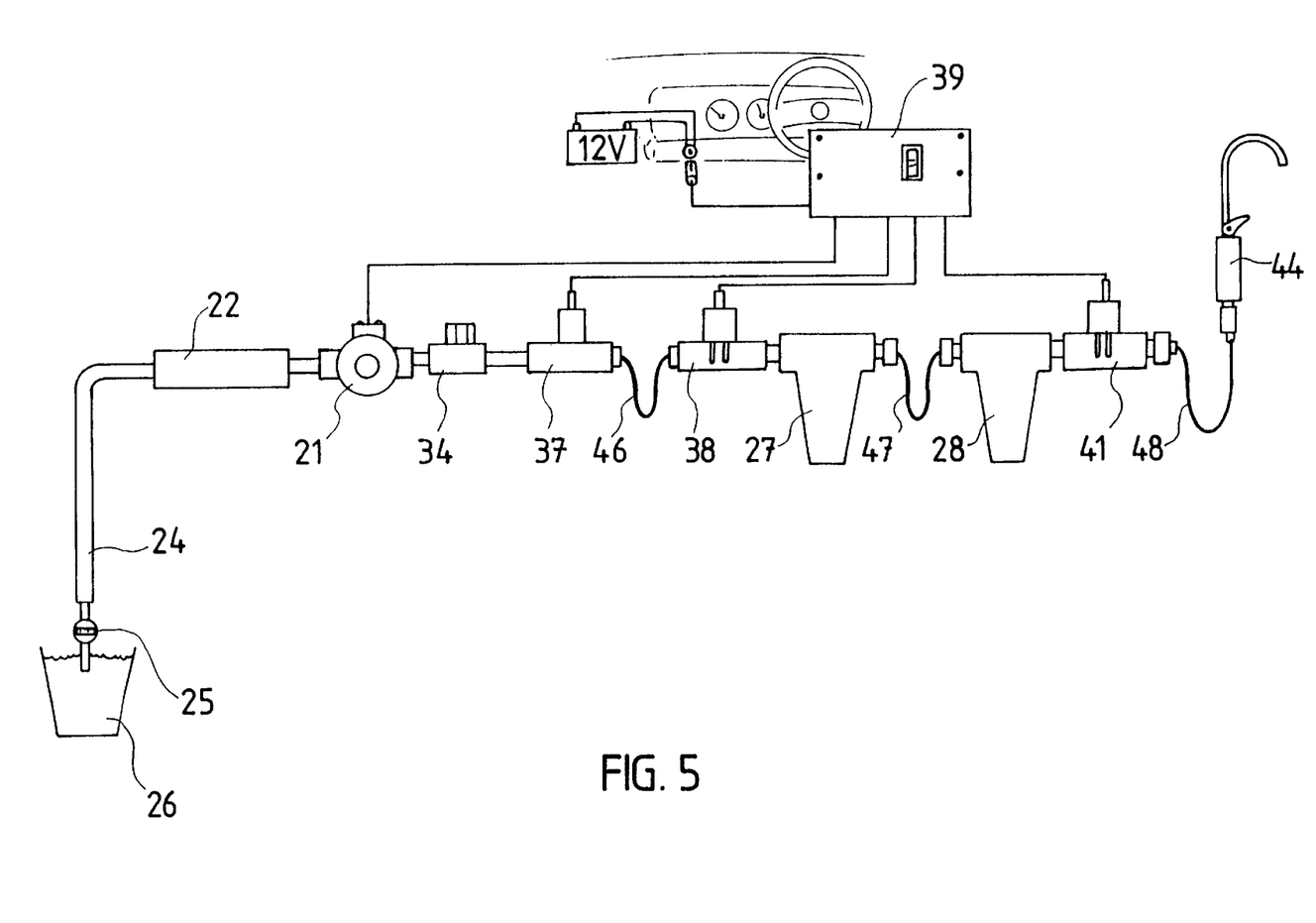
FIG. 5 is a schematic representation of the apparatus of FIG. 1.

A motor pump unit 21 is mounted to the base 11 and a coarse filter unit 22 is connected at one end to the pump inlet 23 and at its other end to a hose 24 which is of a sufficient length to have one end placed in a stream or a bucket of water 26 as shown in FIG. 4 for sucking water into the apparatus for treatment. The primary filter unit 22 is a gauze filter adapted to remove sand, gravel and other relatively large solids. The hose can be removed from the bucket or the stream after use and coiled and stowed within the housing adjacent the central partition, the foot valve 25 being operative to prevent backflow of water from the apparatus.

Two other filter units are mounted downstream of the pump unit, the first being a carbon filter 27 mounted to the central partition on one side and the second being a ceramic filter 28 mounted to the central partition on the other side directly opposite the carbon filter. These filters have identical housings and are mounted in the same manner by a securing plate 29 which is attached to the upper end of the filter housing and releasably connected to the central partition via bolts 30 in key slots 31. The lower ends of the filter housings are restrained from lateral movement by respective collars 32 which extend about the lower ends and are bolted to the base 11. It will be understood that each filter can be easily serviced by simply lifting the filter housing so that the bolts 30 are released from the key slots 31 whereupon the filter housing can be simply lifted from the collar 32. It will be appreciated that ease of servicing of the filters is particularly important if operators are to maintain the apparatus in optimum operating condition. The carbon filter in this embodiment is a four micron dolomite ceramic filter with a design flow rate of three liters per minute and the carbon filter is a five micron powdered activated carbon impregnated cellulose filter having a design flow rate of nineteen liters per minute.

A flow control valve 34 is located between the pump outlet 36 and the carbon filter 27 and is adapted to regulate the flow rate of water from the pump. A flow switch 37 and a silver ion generator 38 are located between the regulating valve and the carbon filter, the flow switch being operative to switch the silver ion generator on and off via a controller 39 which supplies power to the silver ion generator. The controller is connected to a battery by cable 40 and typically the battery would be in a vehicle and the cable 40 would be connected via the cigarette lighter socket.

It will be seen that water entering the carbon filter will have been dosed with silver ions which may lodge in the carbon filter and be effective to prevent the build-up of pathogenic bacteria therein. An additional silver ion generator 41 is located immediately downstream of the ceramic filter 28 and is arranged to discharge directly into the outlet pipe 42. The outlet pipe in turn is connected to a finger tip control on/off valve and a discharge spout 43 is connected to the finger tip control outlet valve 44 and is pivotally mounted to the central partition so that it can be pivoted about a vertical axis for protection by the cover 14.

In use, the apparatus is removed from the boot of the car or the stowage compartment and placed beside the vehicle or even some distance from the vehicle, depending on the length of the cable 40. The cable is then plugged into the cigarette lighter socket and the hose 24 is lowered into a water hole, stream, pond or the like or alternatively water can be collected in the bucket 26 and the hose can be dropped into the bucket. Switch 43 on the controller is then switched on and the pump should run to draw water from the bucket and pressurise the system. Once the flow switch 37 senses flow, it activates the two silver ion generators 38 and 41 so that silver ions are discharged into the water flowing through the system. Once the system is pressurised, a pressure switch 20 incorporated in the pump switches the pump off and upon release of water from the spout 43 the pressure switch restarts the pump. As shown diagramatically in FIG. 5, untreated water enters the apparatus via hose 24 and any solid particles in the water such as sand and gravel are removed by the filter 22 prior to entry of the water to the pump 21. The rate of flow is regulated by the valve 34 and the water then flows through the flow switch 37 and subsequently through the first silver ion generator 38. After being dosed with silver ions, the water enters the carbon filter 27 which should remove odours, tastes and chemical pollutants and then the semi-treated water enters the ceramic filter 28 which in turn should remove any organisms such as protozoans which are not destroyed by the silver ions. The water exiting the ceramic filter is then dosed again with silver ions by the silver ion generator 41 whereupon it is ready for drinking or for bathing. Water can be obtained by simply operating the finger touch control valve 44.

It will be appreciated that the interconnecting hoses 46, 47 and 48 are all fitted to the relevant components by quick release couplings which allow quick and easy servicing and replacement of components. It will also be appreciated that the carbon filter and the ceramic filter are suitably sized to contain about three liters of water so that at any time that a traveller requires a drink, the water in the apparatus should be suitable because it will have been in the system for a sufficient length of time to allow the silver ions to destroy any undesirable bacteria. In this respect it will be understood that the outlet pipe 42 is selected so that the maximum flow rate allowed is in the order of only one to two liters per minute. Of course if greater flow rates are required then additional storage can be added or larger components utilised.

Figure 6:
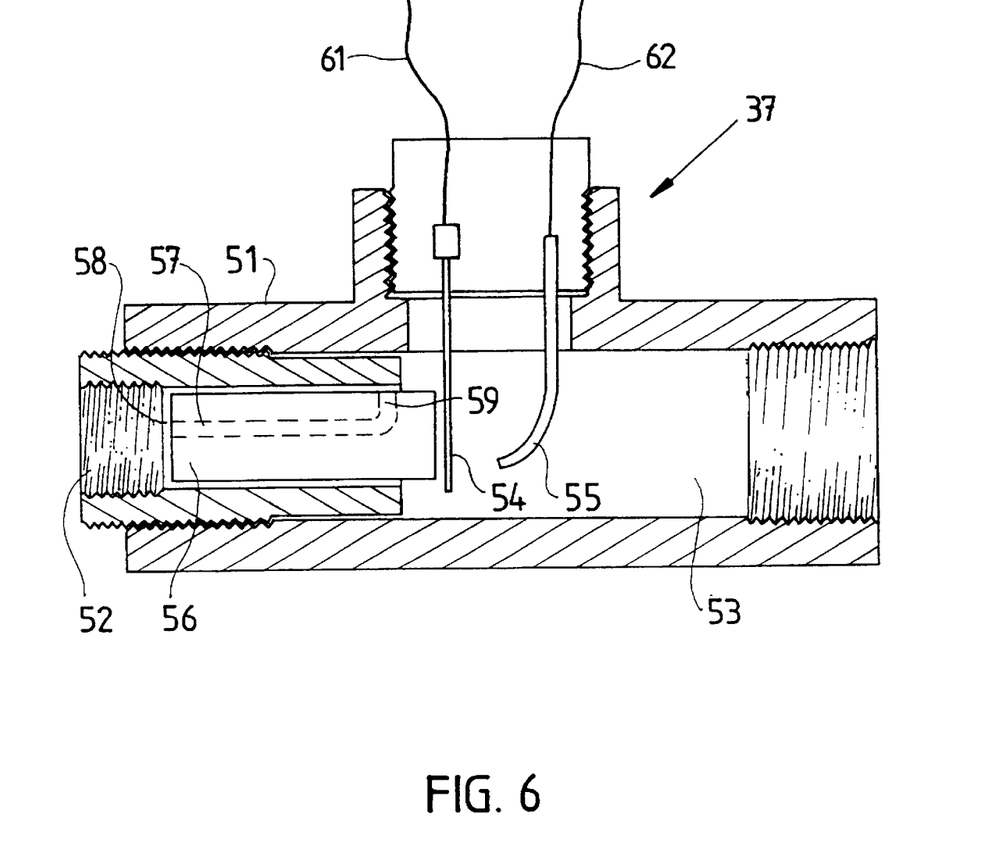
FIG. 6 is a sectional side elevation of a flow switch according to the invention as used in the apparatus of FIG. 1.

The flow switch 37 includes a body 51 having an inlet flow passage 52 and an outlet flow passage 53. A reed 54 and a contact bar 55 are mounted in the outlet flow passage with the contact bar being spaced from and slightly downstream of the reed with the reed being constructed of a flexible metallic material, in this case stainless spring steel, so that it can flex towards and away from the contact bar. A piston 56 is slidably mounted in the inlet passage and located so that it can engage with the reed and force it into electrically conductive engagement with the contact bar to complete a circuit. A flow passage 57 is provided axially in the piston extending from its inlet end 58 and opening into the outlet chamber via a side passage 59. It will be understood that in a no-flow condition the reed forces the piston to a position in which the side passage is sheathed within the inlet passage so that only a very small flow or no flow through the inlet passage can occur whereby the in-flowing water will cause the piston to move towards the outlet passage into engagement with the reed. In this position the side passage opens into the outlet passage and flow through the piston can take place. Moreover the reed engages with the contact bar thus forming a connection between wire 61 and wire 62 while water is flowing. The piston initially prevents flow so that it is subject to the full force of the flowing water and once the piston moves sufficiently to engage the reed with the contact bar, flow through the piston can occur.

Figures 9, 10:
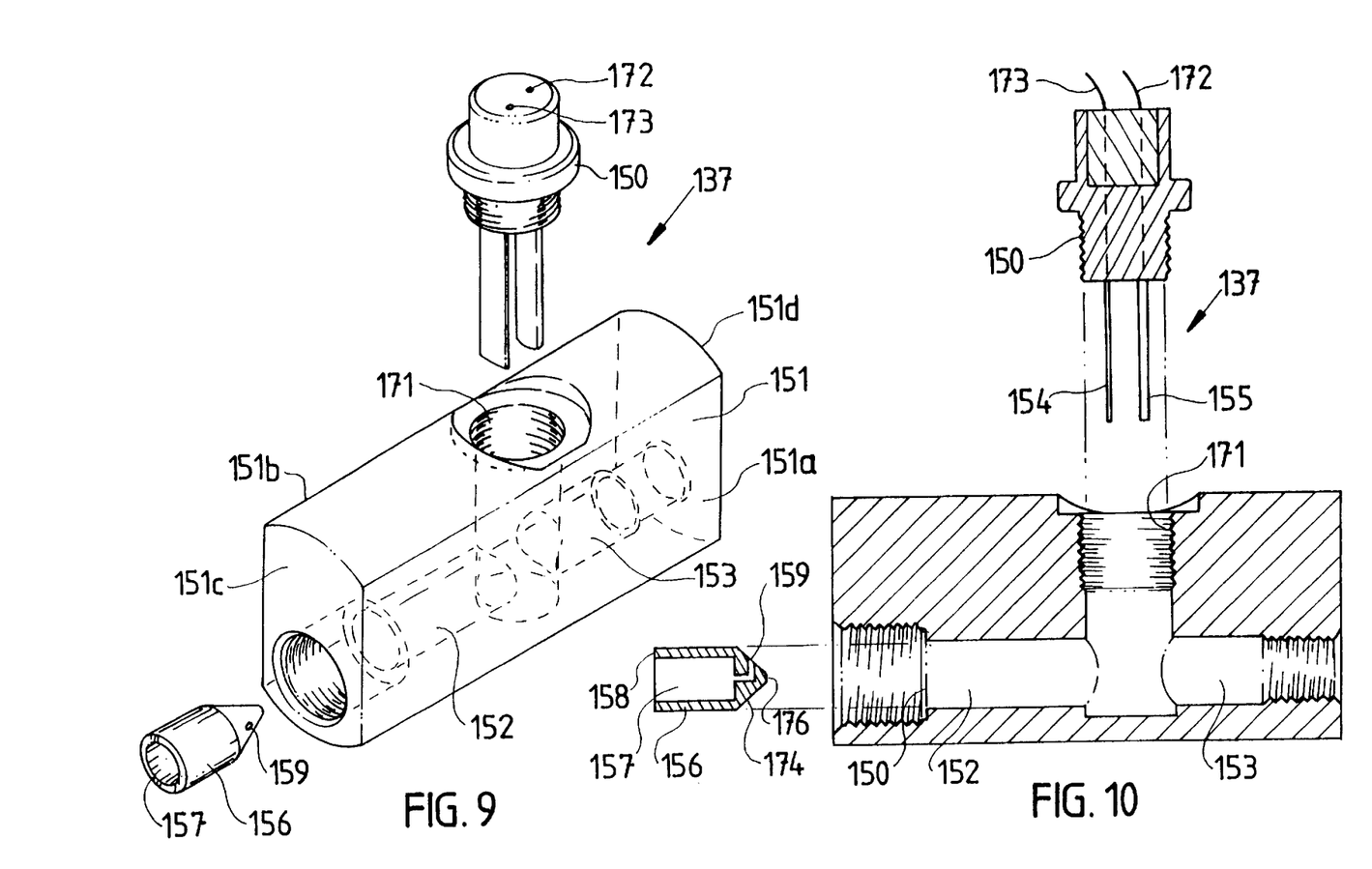
FIG. 9 is a pictorial representation of another flow switch according to the invention which can be used in the apparatus of either FIG. 1 or FIG. 7, with some components in line for assembly.
FIG. 10 is a sectional side elevation of the flow switch of FIG. 9 with the same components in line for assembly.

The flow switch 137 illustrated in FIGS. 9 and 10 operates in a similar manner to flow switch 37 and where appropriate corresponding reference numerals will be used to reference corresponding components but prefaced by a "1". The flow switch includes a body 151 which is substantially a rectangular prism in form having a flat front face 151a and a flat rear face 151b and 2 flat end faces 151c and 151d. A cylindrical flow passage 150 extends through the body from one end to the other providing an inlet flow passage 152 and an outlet flow passage 153. The cylindrical passage is intersected by another passage 171 which is adapted to screwthreadedly receive a switch assembly 150, shown in line for assembly. The switch assembly includes a reed 154 and a contact bar 155 which extend into the cylindrical flow passage downstream of the inlet flow passage in the same manner as in FIG. 6. The switch is screwed into position so that the reed is facing upstream and the contact bar is facing downstream. In this embodiment, the piston 156 has a conical downstream end portion 174 which terminates in an apex 176 which is adapted to make contact with the reed. The flow passage 157 extends from the inlet end 158 of the piston and opens into the outlet passage via a side passage 159 which opens approximately midway along the conical face of the downstream end portion. It will be appreciated that in this form of flow switch, flow is not restricted by the position of the piston in the inlet flow passage 152 as in the case of the flow control valve of FIG. 6.

Figure 7:
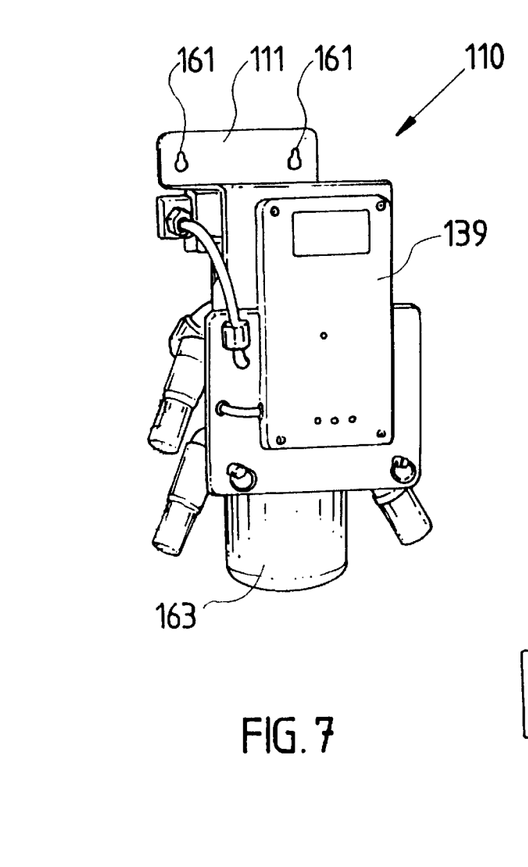
FIG. 7 is a pictorial representation of water treatment apparatus according to the invention for use in an under sink location.
Figure 8:
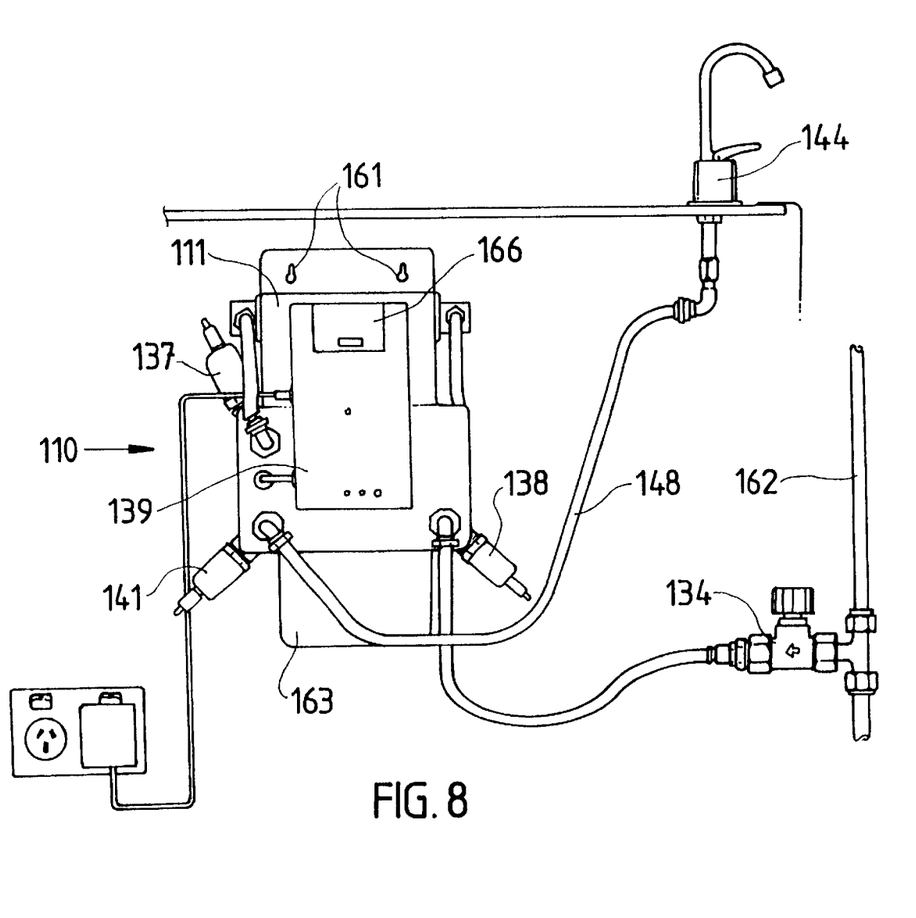
FIG. 8 is a schematic representation of the apparatus of FIG. 7 installed under a domestic sink.

The water treatment apparatus 110 illustrated in FIGS. 7 and 8 is similar to that of FIGS. 1 to 5 in many respects and accordingly where appropriate corresponding reference numerals have been used to reference corresponding components but prefaced by a "1". The apparatus 110 is intended for use with reticulated water systems for example town water, and has a mounting base 111 which has two spaced apart keyholes 161 for securing the base to a gable panel of an under-sink cupboard. A single filtering housing 163 is mounted to the base and contains a carbon filter and a ceramic filter with the same filtering specifications as in apparatus 10. The housing together with the enclosed filters can be easily removed from the base and returned to the factory or other location for servicing. This unit is adapted to be connected directly to the mains pressure supply pipe 162 via a flow control valve 134 which also has a non-return function. It will be appreciated that because of the connection to mains water, neither a pump nor a coarse filter is required. Furthermore, the controller 139 is connected to mains power via a twelve volt transformer instead of being connected to the vehicle battery is in the case of apparatus 10. However, the controller includes a standby battery pack 166 which is arranged to automatically cut in if mains power fails, thereby ensuring that the silver ion generators continue to work in case of a blackout. The apparatus includes a flow switch 137 and two silver ion generators which are mounted to the base and connected in series with the filters in accordance with FIG. 5. This controller has a plurality of different connections for connection of the silver ion generators. It will be appreciated that water conductivity varies from city to city and thus the power supply to the generator needs to be changed to maintain the same quantity of silver ions generated in different water supplies. The plurality of different connections have been selected to cover a range of water conductivities.

While the foregoing description has been given by way of illustrative example of the invention, all other modifications and variations thereto as would be apparent to persons skilled in the art are deemed to fall within the broad scope and ambit of this invention as is defined in the appended claims.

What is claimed is:

1. A flow switch including:
   a body having an inlet passage and an outlet passage;
   a reed and a contact mounted in said body downstream of said inlet passage, said reed being adapted for oscillating movement towards and away from said contact into and out of engagement therewith, and said reed and said contact being constructed of electrically conductive material;
   a piston mounted in said inlet passage for sliding movement along said inlet passage towards and away from said reed, said piston having an upstream end and a downstream end;
   and a flow passage in said piston, said flow passage having an inlet at or adjacent the upstream end and an outlet intermediate said upstream end and said downstream end, the parts being so made and arranged that fluid entering said inlet passage will cause said piston to move in said inlet passage and engage with said reed forcing said reed into electrically conductive engagement with said contact and will flow through said flow passage and be discharged sidewardly of said piston in said body downstream of said inlet passage for discharge through said outlet passage.

2. A flow switch according to claim 1, wherein said piston has a tapered portion adjacent said downstream end and said flow passage outlet is located in said tapered portion.

3. A flow switch according to claim 1, wherein said body is substantially a rectangular prism in form with a single cylindrical passage therethrough with one end portion of said cylindrical passage forming the inlet passage and the other end portion forming the outlet passage.

4. A flow switch according to claim 1, wherein said body is substantially a rectangular prism in form with a cylindrical passage provided in a portion of the body so that fixing apertures may be provided in the remainder the body without the risk of opening into the cylindrical passage.

* * * * *